United States Patent [19]
DeVries et al.

[11] Patent Number: 5,532,817
[45] Date of Patent: Jul. 2, 1996

[54] METHOD OF OPTICAL INSPECTION

[75] Inventors: Robert A. DeVries; Reed A. Shick; G. Thomas Wells; Joseph N. Carr, all of Midland, Mich.

[73] Assignee: The Dow Chemical Company, Midland, Mich.

[21] Appl. No.: 317,089

[22] Filed: Oct. 3, 1994

[51] Int. Cl.$^6$ ............................ G01B 11/02; G01B 15/02
[52] U.S. Cl. ............................................. 356/318; 356/359
[58] Field of Search ................................. 356/318, 359; 528/370, 396; 526/279

[56] References Cited

U.S. PATENT DOCUMENTS

| | | |
|---|---|---|
| 3,617,744 | 11/1971 | Irish . |
| 3,774,030 | 11/1973 | O'Connor et al. . |
| 4,087,685 | 5/1978 | Froot . |
| 4,152,723 | 5/1979 | McMahon et al. . |
| 4,651,011 | 3/1987 | Ors et al. ............................ 250/459.1 |
| 4,774,188 | 9/1988 | Chandross . |
| 4,884,122 | 11/1989 | Eichelberger et al. . |
| 4,929,837 | 5/1990 | DiVita et al. . |
| 4,937,287 | 6/1990 | Dean ...................................... 525/152 |
| 5,040,047 | 8/1991 | Cole et al. . |
| 5,185,391 | 2/1993 | Stokich ..................................... 524/87 |
| 5,310,809 | 5/1994 | Pabon ..................................... 525/289 |

OTHER PUBLICATIONS

Heistand et al., "Cycoten 3022 (BCB) for nonhermetic packaging", Proc. SPIE—Int. Soc. Opt. Eng. (1992), vol. 1847, pp. 584–590.

Charles Seifert, *Circuits Manufacturing*, "A Step Beyond AOI", May 1989, pp. 70–77.

Internaional Application No. PCT/US94/04535, filed Apr. 25, 1994.

*Primary Examiner*—Vasu S. Jagannathan
*Attorney, Agent, or Firm*—Charles J. Enright

[57] ABSTRACT

A method for determining the configuration of a resin portion of an article comprising exposing the article to a light source at a first wavelength and measuring emission of light at a second, different wavelength; wherein the resin contains a moiety containing a structure of the formula:

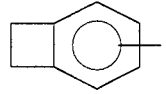

or a moiety which is a reaction product of said moiety in a quantity sufficient to impart fluorescent properties to said resin.

1 Claim, No Drawings

METHOD OF OPTICAL INSPECTION

FIELD OF THE INVENTION

This invention relates to methods of optically inspecting articles and in particular articles containing thin films of benzocyclobutene-containing resins or reaction products thereof.

BACKGROUND OF THE INVENTION

There are a wide variety of resins which may be used as dielectric layers in electronic applications or as thin films in other applications. It is advantageous to be able to determine the configuration of said resins during or after the processing steps used to fabricate a finished article containing the resin. By configuration it is meant such things as the shape, thickness, uniformity of thickness, presence or absence of voids, contamination, mounds of excess material, presence or absence of resin, concentration of the fluorescing species or inclusions in the resin and the like.

A useful method for finding voids, contaminants and excess material is called optical inspection which may be used to find such defects in dielectric layers in microelectronic devices. It is beneficial to use the fluorescent properties of the resin for such inspections. Not all resins are inherently fluorescent at useful wavelengths.

U.S. Pat. No. 5,040,047 discloses a method for enhancing the fluorescence of resins by adding fluorescent dyes such as perylene to the polymer. This adds steps to the process for making the microelectronic articles and the presence of the dye changes the properties of the resin leading to potential deterioration of the properties or requiring a change in the formulation or procedure for using the resin.

SUMMARY OF THE INVENTION

The invention is a method for determining the configuration of a resin portion of an article comprising exposing the article to a light source at a first wavelength and measuring emission of light at a second, different wavelength; wherein the resin contains a moiety containing a benzocyclobutene structure of the formula:

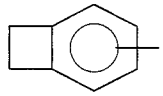

or a moiety which is a reaction product of said moiety in a quantity sufficient to impart fluorescent properties to said resin.

A feature of the invention is the use of a resin containing a moiety containing a structure of the formula:

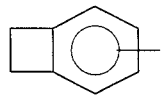

or a moiety which is a reaction product of said moiety in a quantity sufficient to impart fluorescent properties to said resin.

An advantage of the invention is that since the resin which contains the benzocyclobutene moiety or reaction product thereof is inherently fluorescent one does not have to add a dye to the resin to obtain such fluorescence, thus saving process steps and avoiding potential deterioration of resin properties. When the resin which contains the benzocyclobutene moiety or reaction product thereof does not already inherently fluoresce and does not contain a moiety which quenches the fluorescence, the addition of said moiety which is chemically bound to or alloyed into the resin avoids potential property changes encountered with additive formulations.

An additional advantage is that many resins containing the benzocyclobutene moiety or reaction product thereof are transparent and therefore difficult to see with optical inspection equipment operating in the visible light spectrum. In the near ultraviolet spectrum the resin will absorb light making the resin less transparent and permitting properties such as thickness and concentration to be measured.

DETAILED DESCRIPTION OF THE INVENTION

Resins useful in the method of the invention are disclosed in numerous places. Generally, resins containing reacted or unreacted moieties of the formula:

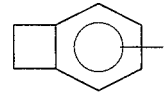

are useful. The

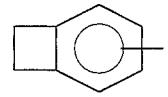

moiety may react to form useful structures by reacting as shown with itself to form moieties, nominally, of the structure shown:

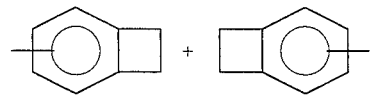

gives

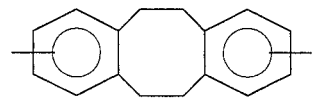

or

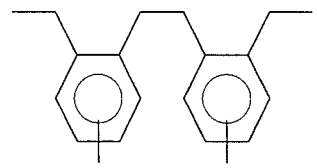

or by reacting with a dienophile such as an ethylenic unsaturation as shown to form moieties, nominally, of the structure shown:

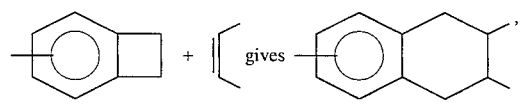

The structures may inherently cause fluorescence or may spontaneously change to form other structures which cause fluorescence. For example, thermal or oxidative degradation or both may lead to dehydrogenation at benzylic sites and the formation of conjugation extended beyond the benzene rings.

Not all reacted benzocyclobutene moieties will form resins which inherently fluoresce. Such non-fluorescing resins are not within the scope of this invention. Exemplary inventive resins are disclosed in the following references.

U.S. Pat. No. 4,708,994 discloses the incorporation of reactive arylcyclobutene groups by means of alkylating or acylating aromatic groups of resins with a molecule containing a reactive arylcyclobutene moiety to provide pendant arylcyclobutene moieties randomly along the polymer backbone. Such resins are then crosslinked and cured during a subsequent heating step and shown to be more solvent and heat resistant.

U.S. Pat. Nos. 4,795,827 and 4,825,001 disclose cyclobutarene ketoaniline monomers that may be used for attaching cyclobutarene groups to polymers or other molecules having amino-reactive functionalities.

U.S. Pat. No. 5,198,527 discloses a carbonate polymer prepared from one or more multi-hydric compounds and having an average degree of polymerization of at least about 2 based on a multi-hydric compound and having terminal benzocyclobutene moieties. Other embodiments of the invention include such carbonate polymers having an average degree of polymerization of from about 2 to about 100 and carbonate polymers having polymerized therein from about 0.01 to about 1 mole of terminal benzocyclobutene-containing compound per mole of multi-hydric compound.

U.S. Pat. No. 4,540,763 discloses polymers of poly(arylcyclobutenes) and how they may be made. U.S. Pat. No. 4,812,588 discloses polymers of poly(arylcyclobutenes) bridged by an organopolysiloxane group and how they may be made.

U.S. Pat. No. 5,034,485 discloses a polymeric composition produced by the reaction of, for example, styrene in a free radical polymerization reaction which is initiated by a cyclobutarene peroxide, wherein the cyclobutarene fragments are incorporated into the polystyrene polymer. A further polymeric product can be produced from the polymeric composition of the free radical polymerization by ring opening polymerization of the cyclobutarene moiety to produce branched, crosslinked or a mixture of branched and crosslinked polymers.

U.S. Pat. No. 4,724,260 discloses polymeric compositions comprising, in polymerized form, a monomer containing a polymerizable arylcyclobutene moiety, and a polymerizable unsaturated alkyl moiety; wherein the monomer is polymerized by subjecting it to conditions sufficient to polymerize the unsaturated alkyl moiety. A related disclosure is U.S. patent application Ser. No. 872,334, filed Jun. 9, 1986, now U.S. Pat. No. 5,360,296 which exemplifies copolymers of vinylbenzocyclobutene and styrene.

U.S. Pat. No. 4,698,394 discloses a solid random copolymer comprising from about 99.99 to about 80 mole percent of a monoalkenyl arene monomer and from about 0.01 to about 20 mole percent, based on total moles of incorporated monoalkenyl arene monomers and olefinic benzocyclobutene monomers, of an olefinic benzocyclobutene of the formula:

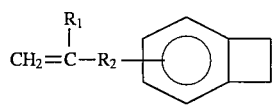

where $R_1$ is hydrogen or $CH_3$ and $R_2$ is $(CH_2)_n$ where n is 0 to 6. Copolymers of vinylbenzocyclobutene and styrene are exemplified.

U.S. Pat. No. 5,077,367 discloses that syndiotactic homopolymers of an arylcyclobutene functional monomer and syndiotactic copolymers of an arylcyclobutene functional monomer and a vinylaromatic monomer are prepared by polymerizing the monomers in the presence of a catalytic amount of a suitable coordination catalyst such as the reaction product of polymethylaluminoxane and a transition metal compound.

U.S. Pat. No. 5,185,391 discloses polymers formed by a side ring opening of an arylcyclobutene moiety such as polymers of

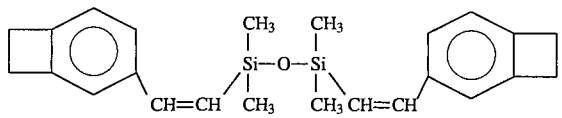

1,3-bis(2-bicyclo[4.2.0]octa-1,3,5-trien-3-ylethenyl)-1,1,3,3-tetramethyldisiloxane (hereinafter DVS), available as a partially polymerized solution in mesitylene from The Dow Chemical Company as Cyclotene® 3022 and an amount of an antioxidant such as a compound of the formula:

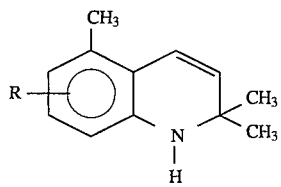

VII sufficient to inhibit oxidation of the polymer.

European Patent Publication 227124 discloses various copolymers of, for example, vinyl benzocyclobutenes and other additional polymerizable materials. These copolymers may be heated to react the benzocyclobutene moieties and crosslink the copolymers.

Monomers of the formulae:

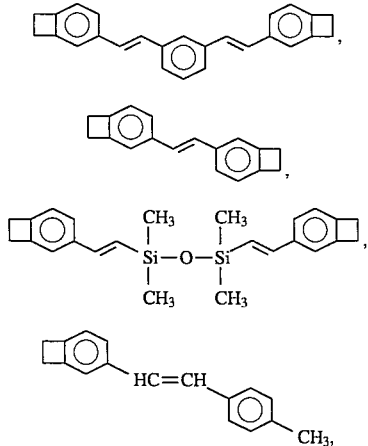

-continued

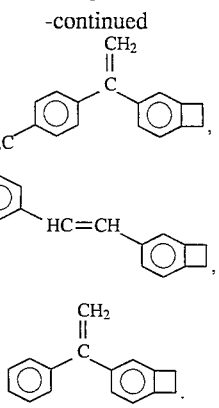

or polymers and copolymers thereof are preferrred.
Monomers of the formulae:

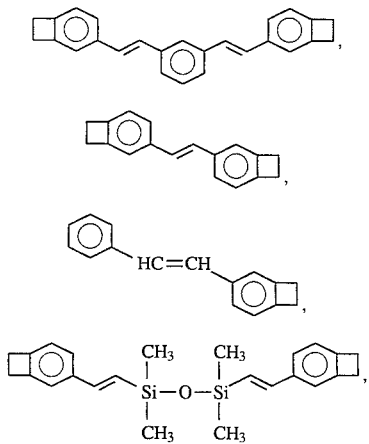

or polymers and copolymers thereof are more preferrred.
Homopolymers of a monomer of the formula

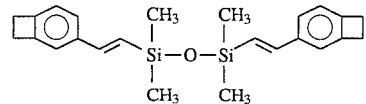

are most preferred.

A number of resins containing either the structure

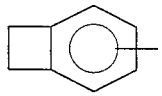

or the reaction product of said structure show fluorescence.

In general, resins containing either the structure

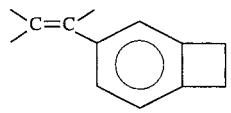

or the reaction product of said structure show strong fluorescence.

The functionality attached to the structure may also quench the fluorescence. Exemplary quenching moieties are ketones and hydroxy functionalities. The property of fluorescence of said structures is most useful when incorporated into resins which do not contain other moieties fluorescing with the quantitative efficiencies of the benzocyclobutene moieties and when said resins do not contain a quenching moiety.

As one aspect of determining the configuration of a resin, one may determine the quantity or concentration of the structure:

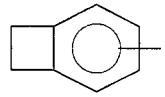

or the reaction product of said structure incorporated into the resin. Said structure may be copolymerized into the resin or may be blended into the resin as an alloy or may be inhomogeneously mixed with the resin.

The strength of fluorescence may be a good indicator of the quantity or concentration of the structure:

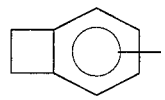

or the reaction product of said structure incorporated into the resin.

Surface defects and thickness of coatings of the resin of the invention over another resin may be measured using the fluorescence. For example, a polycarbonate containing terminal groups of the structure:

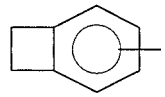

or the reaction product of said structure as described in U.S. Pat. No. 5,198,527 may be coated onto or coextruded with polycarbonates that do not contain said structure. One may determine which side of the article contains the coated or coextruded layer and the thickness or absence of the coated or coextruded layer. This is most beneficial when both resins are optically clear in visible light.

A polycarbonate containing terminal groups of the structure

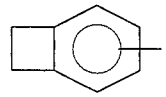

or the reaction product of said structure as described in U.S. Pat. No. 5,198,527 may show a shift in fluorescence. The resin fluorescence at a molar concentration of 0.03/1 benzocyclobutene to bisphenol A has two large maxima at about 370 and 400 nm. The resin fluorescence at a molar concentration of 1/1 benzocyclobutene to bisphenol A has a single large maximum at about 420 nm. One may take this possibility into account when determining benzocyclobutene concentration in a polycarbonate or other resin and make empirical concentration standards against which to measure inspected samples in the range of interest.

A fluorescence spectrometer may be used to screen resins for suitability for fluorescent optical inspection. The fluorescence spectrometer comprises of a broad band light source, a pair of monochrometers, a sample cell and a detector. The light from the source is filtered through the first monochrometer to a wavelength of interest. The filtered light is then directed onto the resin sample. Fluorescent light emitted by the sample is measured at various wavelengths using the second monochrometer. One may measure the ratio of illumination intensity of the source and emitted from the sample to obtain a more meaningful ratio of the intensity of the fluorescence to the source. Not only may one determine if the resin is suitable for fluorescent optical inspection using this method, but one may also optimize the incident light and fluorescent light wavelengths to obtain the most sensitive measure of resin configuration.

Fluorescent optical inspection may be carried out by illuminating a part with a specific wavelength of light and inspecting the part at a different wavelength. The illuminating wavelength is filtered from the light emitted to the detector. A simplified embodiment comprises a mercury lamp which illuminates the part at a wavelength of 365 nm. The emitted light is detected with a stereoscope and a camera. The part is placed in the field of view of the stereoscope and the part is illuminated with the lamp from the side. The crown glass optics of the stereoscope filter out the reflected UV light from the lamp, but allow the longer wavelength fluorescent light from the part to be observed. The camera may be used to record the emitted light.

One may use conventional, commercially available, optical inspection devices for such optical inspection. Typically these devices use a bright line source, a broad band pass filter and some form of machine vision. The source of illumination may be a laser or atomic line emission source. The use of a line source eliminates the need to prefilter the light to get only the wavelength of interest. The emission filter system is chosen to block only the illuminating light wavelengths, while allowing fluorescent light of any wavelength to pass to the detector. The detector may be an array type so that computer logic can be applied to pass or reject parts.

Preferably the illuminating and fluorescent light wavelengths are both in the near UV. Preferred illuminating wavelengths are 337.5, 356.4 or 408 nm of a $Kr^+$ laser; 351.1 or 383.8 of an $Ar^+$ laser; 325 or 442 nm of a He/Cd laser or 254 or 365 nm of a mercury vapor lamp.

Fluorescence is the absorption of light at one wavelength and the re-emission of that energy at a different, longer wavelength. Fluorescent illumination provides an advantage in that one may illuminate with one wavelength and detect at a different wavelength of light. Fluorescence more easily distinguishes between resin and inclusions such as metal circuitry which do not fluoresce. If the incident and reflected light have the same wavelength, the only parameter distinguishing portions of the article being seen is the reflectance. Reflectance of metal inclusions may vary depending on the amount of oxide on the surface.

There are a number of commercial automated systems available for optical inspection of laminate boards and multichip modules. Some commercial sources are Optrotech Inc. of Billerica, Mass. or Orbot Inc. of Santa Ana, Calif. Photometrics Ltd. of Tuscon, Ariz. produces the "Star I CCD™" imaging system. This system may be attached to a stereo microscope for magnification. The image produced may be stored on a personal computer and enhanced with commercially available software programs with features such as color enhancement, line and edge signal filtration, contrast adjustment, image magnification and the ability to produce images of the difference between two objects. An example of such a program is IPLab Spectrum™ software from Signal Analytics Corp. of Vienna, Va.

Automated optical inspection may be divided into three basic steps: image acquisition, logic and processing effect data. Image acquisition—the creation of an accurate digital replica of a circuit pattern is most important. The article to be inspected is illuminated by a light source and the emitted light is detected usually by a camera which can convert the image to digital format.

U.S. Pat. No. 4,152,723 provides a detailed description of an optical inspection method for circuit boards. A beam of light energy scans, in a predetermined pattern, a surface of the board comprising a pattern of a metallic conductor disposed on an insulating substrate. The beam has an energy level high enough to excite detectable fluorescence in the surface of the insulating substrate. The fluorescence is selectably detected by means sensitive to the wavelength of the fluorescence and is converted to a binary signal which indicates whether the beam is incident on the fluorescing substrate or on the non-fluorescing metallic conductors. The binary signal is then synchronized with the scanning of the beam such that a binary image representation of the board's surface is generated.

Image processing options expand the ability to detect and identify defects in thin films. A digital system may be used to compare a desired image, generated using a CAD image or an actual functioning (golden board) with the board being inspected. The system may be programmed to show only the differences between the two images and to distinguish between the types of defects. Films could be rejected automatically based on the number of areas with too little or too much resin.

With a Fourier transform of the difference between the two images, the type of defect could be identified. For more sensitive processing than differentiation, the Fourier transformed image can be examined for spatial frequencies characteristic of defects. After filtering the transform for defects of interest, an inverse transform would consist of an image of only the defects.

The types of configurations one may determine using the fluorescent optical inspection method of the invention are thickness of the resin, coating uniformity, particulate contamination, pin holes, gels, bubbles, clearing of vias, cracking, blisters, wrinkles and delamination.

The thicker the resin, the more strongly it emits and thus one may determine the thickness or uniformity of thickness. The more concentrated the resin is in terms of the

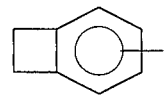

moiety or reaction product thereof, the more strongly it will emit and thus the concentration of that moiety may be determined. Contaminant particles show as dark spots on the picture. Pin holes show as dark spots surrounded by a bright ring because of totally internally reflected light that is emitted at the edges of the pin hole. Particles of excess resin or other lumps of excess resin in the film or on the surface of the film show as light spots in the picture. Cracks show as dark lines with bright edges. Gels, blisters and wrinkles show as brighter areas. Delaminations show as darkened areas.

ILLUSTRATIVE EMBODIMENTS

The following examples are given to illustrate the invention and should not be interpreted as limiting it in any way. Unless stated otherwise, all parts and percentages are given by weight.

EXAMPLE 1

Cyclotene® 3022 resin is spin coated on four inch silicon wafers to give a 5–10 micrometer thick coating after evaporation of solvent and complete curing of the resin. The coatings are illuminated by a mercury vapor lamp with the beam passing through a monochrometer at a wavelength of 365 nm. Polaroid® pictures of the image seen through a stereoscope are taken. The film is sensitive to the fluorescing wavelengths.

Dust particles show as dark spots on the picture. Pinholes show as dark spots surrounded by a bright ring because totally internally reflected light is emitted at the edges of the pin hole. Particles of excess resin or other lumps of excess resin on the surface of the film show as light spots in the picture.

Homopolymers of monomers of the formulae:

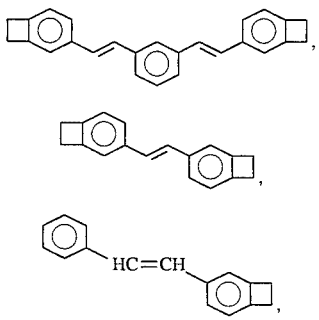

yield similar results.

EXAMPLE 2

A high density multichip module with Cyclotene 3022® resin used as the interlayer dielectric is photographed using both visible white light and UV light from a 365 nm source. The metal structures show up clearly in both photographs. It is difficult to differentiate the different layers of metal in the visible light photograph. The resin is transparent to visible wavelengths. In the near UV, since the resin fluoresces, the thicker the dielectric layer, the more strongly emitting the portion of the image. This permits differentiation between different layers of metal circuitry.

EXAMPLE 3

A series of wafers are prepared. One half of the area of some silicon wafers is sputter coated with aluminum metal. The wafers are then coated with a resin formulation containing a partially polymerized resin of the monomer of the formula:

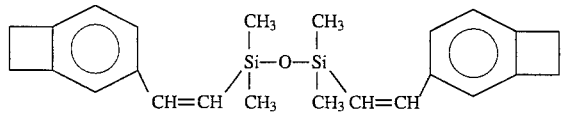

a photocrosslinking agent, an antioxidant and a solvent. The solvent is evaporated to leave a resin layer, nominally, 10–12 micrometers thick. The resin layer is photopatterned by exposing and developing it with a development solvent and thermally curing it. The resin layer is patterned with vias or through holes 1, 2, 5, 10, 15, 25, 35, 50, 75 and 100 micrometers across in both round and square shapes.

The wafers are held under a mercury UV lamp at arms length and visually inspected. Some of the resin is not competely removed from the smaller vias by the development solvent. Residual resin is apparent even when less than one micrometer thick. Residual resin 0.1–0.3 micrometers thick is visible in the bottom of the smaller vias. Cracks, streaks and other defects are observed on some wafers made using a nonoptimized process.

The wafers are inspected in a light-tight box to exclude room light. Images are taken at 39× and 115× magnification using a stereo microscope with a T adaptor and a Star I CCD™ imaging system. The image is transferred via an IEEE-488 interface to a Macintosh IIci PC loaded with IP Spectrum™ software. The image is stored on a PC or mainframe computer. The image may be processed by contrast adjustment, digital filtering, color enhancement or any combination thereof. Any necessary hard copy of the image may be made with an existing compatible printer.

Images are taken while the wafers are illuminated with diffuse white light, illuminated with a line filtered 365 nm mercury UV lamp or illuminated with the mercury lamp with the box open to let in room light. Diffuse white light shows shadows of vias down to 25 micrometers and hints of vias at 15 micrometers. One is not able to determine whether the smaller vias are open. The 100 and 75 micrometer vias appear to be open. It is difficult to tell whether the 50 micrometer vias are open.

When illuminated with the line filtered 365 nm UV lamp open vias appear as dark areas in the otherwise light emitting resin. The 50, 75 and 100 micrometer vias appear to be open. The 25 and 35 micrometer vias are apparent but it is not clear whether they are open due to the low magnification.

With the one side of the box open, one is able to see via features as small as two micrometers. The mercury lamp is at an angle. One may obtain clearer images of smaller features by moving the lamp to a position perpendicular to the feature of interest.

What is claimed is:

1. A method for determining a thickness or uniformity of thickness of a resin portion of an article or the presence of cracks, voids, mounds or contaminants comprising exposing the article to a light source at a first wavelength in the near UV and measuring emission of light at a second, different wavelength; wherein the resin is a homopolymer of a monomer of the formula:

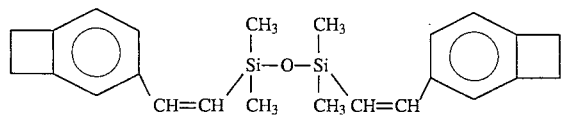

and wherein the sole source of fluorescence is the resin.

* * * * *